United States Patent [19]

Eyre et al.

[11] 4,395,783

[45] Aug. 2, 1983

[54] METHOD OF MAKING AN ARTIFICIAL LEG

[75] Inventors: Harry Eyre, Alton; James A. Wood, Farnham, both of England

[73] Assignee: Vessa Limited, Hampshire, England

[21] Appl. No.: 283,865

[22] Filed: Jul. 16, 1981

[30] Foreign Application Priority Data

Jul. 16, 1980 [GB] United Kingdom ................. 8023308
Jul. 16, 1980 [GB] United Kingdom ................. 8023309

[51] Int. Cl.³ .............................................. A61F 1/08
[52] U.S. Cl. ................................................. 3/30; 3/2
[58] Field of Search ................... 3/2, 6, 7, 22, 30, 31, 3/32, 33

[56] References Cited

U.S. PATENT DOCUMENTS

| | | | |
|---|---|---|---|
| 2,440,075 | 4/1948 | Campbell | 3/33 |
| 2,556,525 | 6/1951 | Drennon | 3/32 |
| 3,538,516 | 11/1970 | Bailey et al. | 3/31 X |
| 3,551,914 | 1/1971 | Woodall | 3/6 |
| 3,706,465 | 12/1972 | Olowinski | 3/2 X |
| 3,956,775 | 5/1976 | Moore | 3/2 |
| 3,982,278 | 9/1976 | May | 3/30 |
| 4,089,072 | 5/1978 | Glabiszewski | 3/6 |
| 4,177,525 | 12/1979 | Arbogast et al. | 3/7 |
| 4,283,800 | 8/1981 | Wilson | 3/22 X |

Primary Examiner—Richard J. Apley
Assistant Examiner—David J. Isabella
Attorney, Agent, or Firm—Pollock, Vande Sande & Priddy

[57] ABSTRACT

An artificial leg is assembled from a thigh member and a selected one of a plurality of preformed modular endoskeletal shin members each having an identical knee support member and ankle attachment member but differing in length of shin tube. A cellular plastics cosmesis is moulded onto the shin member. A foot may be attached to the shin member with an intermediate disc bearing differentially spaced circumferential teeth on its upper and lower faces which locate in sockets in the ankle attachment member and in the foot to permit fine adjustment of the position of the foot relative to the shin member.

2 Claims, 6 Drawing Figures

METHOD OF MAKING AN ARTIFICIAL LEG

FIELD OF THE INVENTION

The present invention relates to a method for making an artificial leg which is assembled from a stock of modular components which can be held by a limb fitting center and which can be assembled rapidly and inexpensively.

By the present method it is anticipated that patients will be able to be fitted with a leg in the course of a single working day, and the leg has sufficient cosmesis and in the embodiment described operates sufficiently well to be accepted for medium or long term use by relatively inactive patients such as geriatric patients. Accordingly the need to fit such patients with a pylon and then to fit them with a definitive leg can be avoided.

SUMMARY OF THE INVENTION

In one aspect the invention provides a method of making an artificial leg which comprises:

providing a thigh member having a stump socket at its upper end supported on struts from a knee joint member;

providing a plurality of preformed endoskeletal shin members each having an identical knee support member at its upper end, an identical ankle attachment member at its lower end, a shin tube rigidly connecting the knee support member and the ankle attachment member and a generally tubular cosmesis of cellular plastics material moulded onto the shin tube between the knee support member and the ankle attachment member, the shin tubes differing in length within a permitted range of length values;

forming a pivoted knee joint in which load is transmitted from the knee joint member to the knee support member; of a selected one of the shin members of a length; and connecting a foot to the ankle attachment member.

A preferred method of forming the stump socket involves the steps of moulding a plurality of generally tubular socket blanks from sheet plastics material, the blanks having adjoining unconnected edges defining a vertical split in the socket blank;

fitting a selected one of the socket blanks to the stump and cutting the adjoining edges so that the socket blank fits around the stump with the cut edges abutting;

fastening the cut edges to form the socket; and fastening the socket to the struts.

Preferably the endoskeletal shin members are formed by securing a knee support member and an ankle attachment member to opposed ends of a shin tube, placing the assembly in a mould internally shaped to simulate the shin portion of a leg and introducing into the mould a resin composition which foams and cures to a cellular plastics material.

The leg substantially as described below and illustrated in the drawings is believed to be novel per se.

In another aspect the invention relates to an assembly of a shin member and a foot for an artificial leg, wherein there is provision for variation of the angular position of the foot relative to the leg in very small rotational increments.

The present invention provides an assembly of a shin member and foot for an artificial leg having a disc sandwiched between them, the upper face of the disc and the shin member locating by engagement of a first set of circumferentially spaced teeth in a first corresponding set of sockets and the lower face of the disc and the foot locating by engagement of a second set of circumferentially spaced teeth in a second corresponding set of sockets, and means securing the foot to the shin member against movement longitudinally apart whereby the foot is located in a fixed predetermined angular position relative to the shin member.

Preferably the foot is secured to the shin member by a bolt which passes through a hole in the disc and locates in an internally threaded anchorage point at the base of the shin member. The angular spacing of the teeth of the first and second sets is preferably slightly different in order to obtain a differential effect. The foot preferably comprises a keel member of rigid material moulded into a body of cellular plastics material, an ankle base member above the keel member and fixed to the shin member and transverse pivot means interconnecting the keel member and the ankle base member.

BRIEF DESCRIPTION OF DRAWINGS

An embodiment of the invention will now be described, by way of example only, with reference to the accompanying drawings, in which.

DETAILED DESCRIPTION OF PREFERRED EMBODIMENTS

Figure 1:
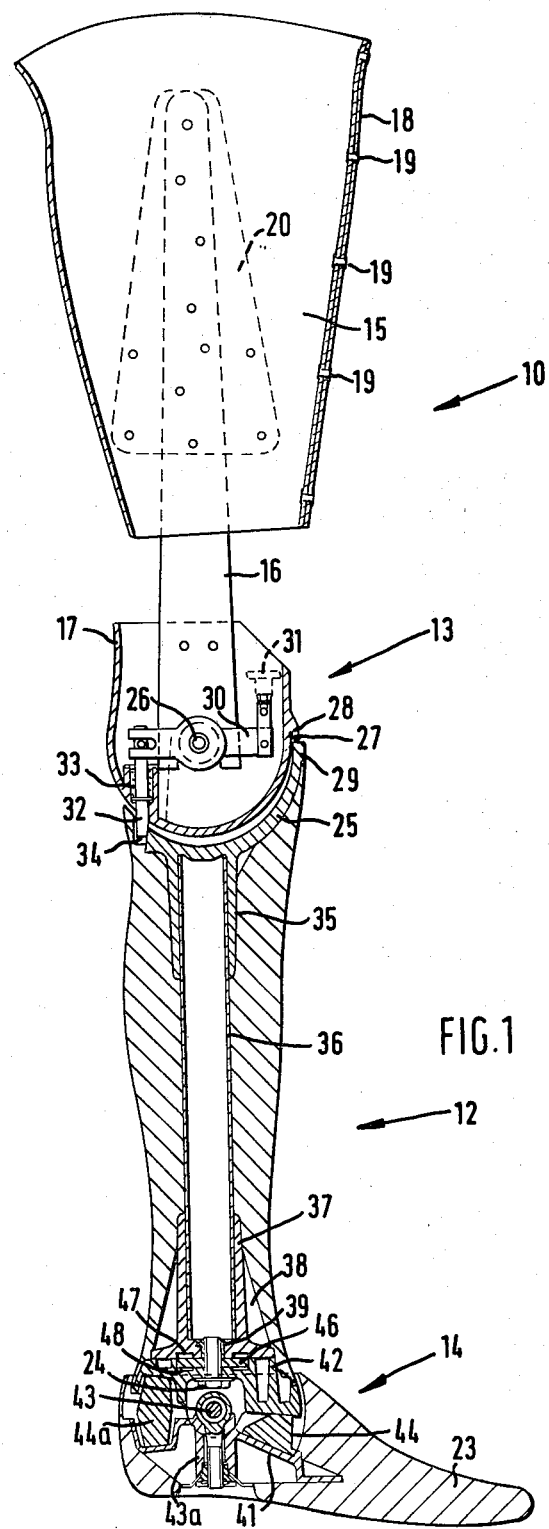
FIG. 1 is a side view in vertical section of an artificial leg according to the invention.

The leg shown in FIG. 1 has a thigh member indicated generally by 10 and a shin member indicated generally by 12 interconnected by a knee structure indicated generally by 13. A uniaxial foot indicated generally by 14 and believed to be of novel construction is fitted to the lower end of the shin member 12, but is optional and the needs of some patients may be met by a conventional solid ankle cushion heel (SACH) foot.

The thigh member 10 includes a load bearing stump socket 15 which is supported on struts 16 whose lower ends are secured in a knee fairing 17 of metal or preferably of a filled thermoplastics material such as glass-reinforced nylon. The stump socket 15 is formed from a piece of thermoplastics sheet of a selected one of a range of standard sizes which is rough-formed to the approximate dimensions and shaped by vacuum or drape moulding. The resulting socket blank is fitted to the patient and the adjoining split edges can be trimmed to alter the angle of the socket in either direction and to alter the socket circumference. After the edges have been cut they are butted together and a plastics strip 18 is laid over them by rivets 19 whereby there is produced a socket to fit an individual stump. Alternatively butted edges of the stump socket may be welded together. The top ends of the struts 16 are secured to the outer surface of the stump socket 15 using wing plates 20 of aluminum as reinforcement and the lower ends of struts 16 are riveted to the inner face of the knee fairing 17.

The knee fairing 17 has a generally hemispherical lower end as shown and is supported by a knee socket 25 forming part of the shin member 12 which is also made of a glass filled nylon and has a part spherical inner top surface complementary to the knee fairing. A transverse knee pivot shaft 26 interconnects the fairing 17 with the socket 25. Forward travel of the thigh member 10 relative to the shin member 12 beyond the straight position illustrated is prevented by abutment of a rubber buffer 27 supported at an anterior portion of the knee fairing by a buttress member 28 with a thickened load-accepting top anterior portion 29 of the socket 25. A pivoted link member 30 operated by a release handle 31 on the exterior of the knee fairing retracts a locking plunger 32 against the action of coil spring 33 from engagement with a locking face 34 in a posterior portion of the knee socket 25 thereby allowing flexion of the thigh member 10 relative to the shin member 12.

It will be understood that the uniaxial knee joint shown could for certain patients be replaced by a polycentric joint having a 4-bar or 6-bar linkage or by a stabilized knee joint of the general kind described in U.K. Pat. No. 874,327.

The shin member 12 is, as may be seen, of the endoskeletal type and has the knee socket 25 previously referred to secured to a shin tube 36 (eg. by riveting it into a depending boss 35). The lower end of the tube 36 is secured in an upstanding boss 37 forming part of an ankle attachment member 38 also of filled thermoplastics material having a generally planar lower face in which there is a centrally positioned vertically directed internally threaded metal insert 39 for attachment of a uniaxial foot as described below. A cosmesis in low density elastomer is formed surrounding the shin tube 36 between the socket 25 and the attachment member 38. The shin assembly 12 is formed by cutting the tube 36 to length and riveting socket 25 and attachment member 37 to opposed ends thereof, after which the assembly is placed in a mould and a foamable plastics composition is introduced into the mould and allowed to cure. This structure of the shin member has the advantage that it can readily be provided in the form of a plurality of preformed shin members each of one of a range of possible standard lengths, and a limb fitter making a leg for a particular patient at a limb fitting center can select the appropriate shin member for the particular patient who he is fitting. Hitherto the shin members have been made individually and the cosmesis has also been made and shaped individually which is a laborious process. The provision of shin members in stock sizes which can be stored at a limb fitting center in combination with the stump socket forming technique previously described enables a patient to be fitted with an artificial leg during the course of a one-day visit to a limb fitting center and is advantageous to the patient who is spared the trouble of repeated visits to a limb fitting center and delay in receipt of his artificial leg, and has self-evident cost advantages.

The shin member 12 is fitted with a uniaxial foot 14 made up of a body 23 of a low density microcellular elastomeric material in which is moulded a relatively rigid keel 41 of glass-reinforced plastics material. An ankle base 42 also of glass-reinforced plastics material is secured at its upper face to the ankle attachment member 38 and at its lower face is pivoted to the keel 41 about a transverse ankle pivot 43 which is held within a tee-bolt 43a with intermediate bearing bushes. An instep buffer 44 and a heel buffer 44a both of natural or synthetic rubber are located respectively between anterior and posterior portions of the ankle base 42 and the keel 41 to provide the appropriate degree of resistance to flexion of the foot 14 relative to the shin member 12 from a normal position which they define. The ankle base 42 is secured to the ankle attachment member 38 against movement longitudinally apart by means of a bolt 24 which is engaged in the threaded insert 39 and angular location of the foot 14 relative to the shin member 12 is achieved by means of a disc 46 having rows of circumferentially spaced teeth 47, 48 on its upper and lower faces which locate in respective sockets in attachment member 38 and an ankle base 42 as described in more detail below. The ankle base may be selected from a range of standardized injection-moulded ankle bases each having different lower face angles so that variation in heel height can be accommodated. The full range of ankle bases can be produced in a single mould, pads defining the desired angle for the lower face of the ankle base being inserted into the mould before the moulding operation is carried out.

Figure 2:
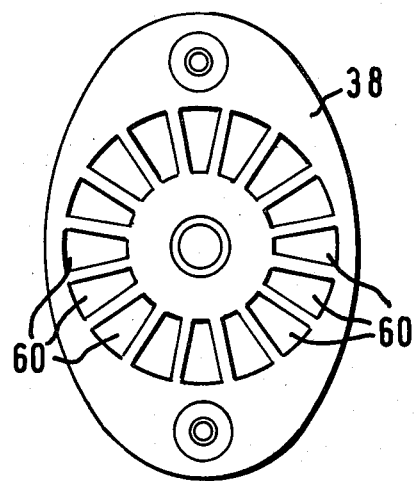
FIG. 2 is an enlarged underneath view of an ankle attachment member used in the shin portion of the leg illustrated in FIG. 1.
Figure 4A:
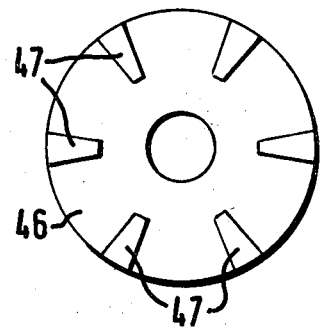
FIGS. 4a, 4b and 4c are top, side, and underneath views on an enlarged scale of a locating disc which fits between the ankle base and the ankle.
Figure 4B:
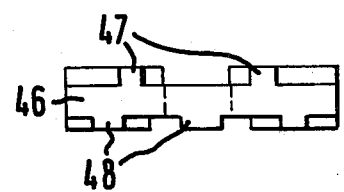
Figure 3:
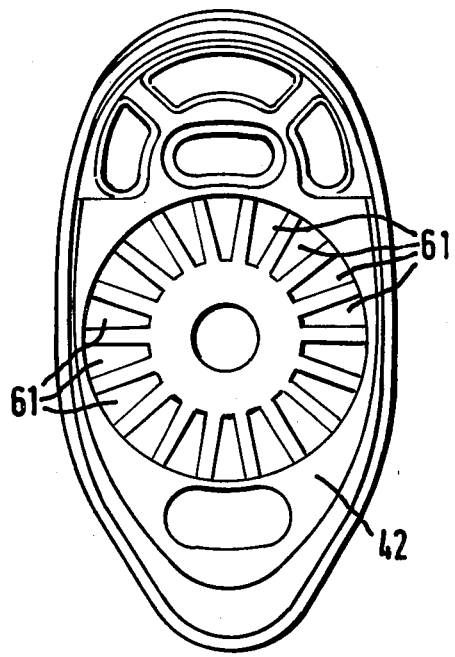
FIG. 3 is an enlarged plan view of an ankle base interconnecting the shin portion of the leg to the foot.
Figure 4C:
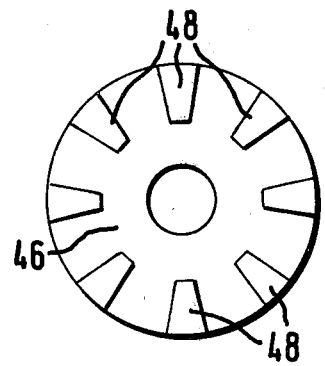

The ankle attachment member 38 of FIG. 2 is formed with a plurality of recesses 60 disposed about the circumference of a circle to receive the teeth 47 (FIGS. 4a and 4b) of the disc 46. It will be noted that the ankle attachment member 38 has eighteen recesses at equal angular spacings of 20° and the top face of the disc 46 has six teeth at angular spacings of 20°. The ankle base 42 (FIG. 3) is formed with sixteen sockets 61 disposed at equal angular spacings of 22.5° and the disc 46 is formed on its lower face with eight teeth 48 at angular spacings of 45° (FIGS. 4b and 4c). This differential spacing of the teeth on the upper and lower faces of the disc 46 enables the angular position of the disc 46 relative to the ankle attachment member 38 and the angular position of the ankle base 42 relative to the disc 46 to be combined so that the foot 14 assumes any one of a large range of closely spaced angular positions relative to the anterior-posterior plane of the leg. The disc 46 is firmly held in position by the bolt 24 and the insert 39, and engagement of the teeth 47, 48 in their respective sockets 60 and 61 positively locates the foot 14 at a desired toe-out angle. The teeth provide a relatively large bearing surface well spaced from the bolt 24 and therefore in a good position to resist turning forces on the foot 14.

We claim:

1. An assembly of a shin member and foot for an artificial leg having a disc sandwiched between said shin member and foot, the upper face of the disc and the shin member locating by engagement of a first set of circumferentially spaced teeth in a first corresponding set of sockets and the lower face of the disc and the foot locating by engagement of a second set of circumferentially spaced teeth in a second corresponding set of sockets, said second set of teeth having a different angular spacing from said first set of teeth to permit the making of fine adjustments in the positions of said shin member and foot relative to one another, and a bolt passing through a hole in said disc and locating in an internally threaded anchorage point at the base of the shin member to secure the foot to the shin member against movement longitudinally apart whereby the foot is located in a fixed predetermined angular position relative to the shin member.

2. An assembly according to claim 1, wherein the foot comprises a keel member of rigid material moulded into a body of cellular plastics material, an ankle base member above the keel member and fixed to the shin member, and transverse pivot means interconnecting the keel member and the ankle base member.

* * * * *